United States Patent [19]

Bridge et al.

[11] Patent Number: 5,059,171
[45] Date of Patent: Oct. 22, 1991

[54] BUBBLE DETECTION SYSTEM

[75] Inventors: Burton E. Bridge, Ventura; William T. Lemons; John S. Thompson, both of Oxnard, all of Calif.

[73] Assignee: BOC Health Care, Inc., New Providence, N.J.

[21] Appl. No.: 541,564

[22] Filed: Jun. 21, 1990

[51] Int. Cl.$^5$ ............................................. A61M 31/00
[52] U.S. Cl. ......................................... 604/67; 604/122
[58] Field of Search ...................... 604/122, 65, 66, 67, 604/118; 128/DIG. 12, DIG. 13

[56] References Cited

U.S. PATENT DOCUMENTS

| | | |
|---|---|---|
| 3,915,155 | 10/1975 | Jacobson et al. |
| 4,502,488 | 3/1985 | Digeronimo. |
| 4,828,545 | 5/1989 | Epstein et al. ........................ 604/67 |
| 4,846,792 | 7/1989 | Bobo, Jr. et al. ................. 604/67 X |
| 4,874,359 | 10/1989 | White et al. ...................... 604/67 X |
| 4,898,579 | 2/1990 | Groshong et al. .................... 604/67 |
| 4,919,650 | 4/1990 | Feingold et al. ....................... 604/67 |

FOREIGN PATENT DOCUMENTS 0328162 10/1984 European Pat. Off.

Primary Examiner—John D. Yasko
Attorney, Agent, or Firm—Roger M. Rathbun; Larry R. Cassett

[57] ABSTRACT

A bubble detection system for use in a fluid delivery line leading to a patient for automatic delivery of a fluid. The system monitors a parameter indicative of compressibility of the fluid being delivered and compares that monitored parameter with a known value of the same parameter using a relatively incompressible fluid. If the fluid being delivered is more compressible by a predetermined amount, the system recognizes the existence of a bubble and stops the further movement of fluid toward the patient and reduces the pressure in the fluid delivery line upstream of the bubble to prevent the bubble from progressing further toward the patient. The parameter may include pressure in the fluid delivery line, force required to deliver the fluid or motor current in the event an electric motor is used in delivering the fluid.

26 Claims, 3 Drawing Sheets

BUBBLE DETECTION SYSTEM

BACKGROUND OF THE INVENTION

This invention relates to a system for detecting bubbles in a fluid line leading to a patient and, more particularly to an improved means of protecting against the introduction of bubbles into such patient.

One of the common procedures during operations is the monitoring of cardiac output. Although some systems have been proposed to carry out noninvasive cardiac output, by far the most common method is to utilize thermodilution. The method is invasive and utilizes a catheter, such as a Swan Ganz catheter, that is positioned within the heart. A liquid having a known temperature, normally chilled, is introduced through the catheter into the right atrium and a temperature sensor, positioned in the pulmonary artery senses the change in temperature of the blood exiting the heart. By a correlation of time and temperature drop, a measurement of cardiac output can be readily calculated.

In common practice, the injection of the cold bolus of liquid is carried out manually by attending personnel through use of a syringe that has been chilled to the appropriate temperature.

In recent years, there have been attempts to automate the injection of the chilled liquid to improve consistancy and to alleviate the workload of personnel in the operating room. In such systems the bolus of chilled liquid may be automatically introduced by means of a stepper motor controlled syringe or linear actuator. That automated process is referred to as Automated Thermo Dilution (ATD) and is beginning to be used in hospital operating rooms. An example of an ATD system can be seen in U.S. Pat. No. 4,502,488 of Digeronimo.

As a further recent development, the time/temperature relationship used in determining cardiac output can be obtained by an injectless type of system such that the cold liquid injectate does not actually enter the patient's bloodstream. Instead, the cold liquid is contained in a sheath within the catheter, such that heat transfer with respect to the cold liquid and the blood takes place but the liquid is, at all times, isolated from the blood stream. The system is referred to as a Continuous Cardiac Output (CCO) method and is currently undergoing evaluation.

In either system, ATD or CCO, the chilled liquid is pumped by automatic means, thereby eliminating the use of attending personnel to manually operate a syringe. One difficulty with replacing an operator however, is that the injectate systems thereby function without visual observation. Accordingly, a problem can arise by a bubble being present in the chilled injectate and which could move unobserved toward the patient. In the case of ATD, that bubble will, if undetected, ultimately be injected into the patients vascular system where it can cause damage to the patient. The possibility is somewhat more remote in the case of CCO since the system would require a leak somewhere for a bubble to actually enter the patient's bloodstream, however, in the case of medical operations, it is obviously better to provide maximum protection against potential harm to a patient.

There are bubble detectors commercially available that can be used in such injectate systems and many rely upon some photoelectric or ultrasonic means of sensing the bubble. An example of the use of such bubble detectors can be found in U.S. Pat. No. 3,915,155.

A difficulty with such detectors is, however, that the bubble, to be detected, must progress beyond the automatic injection means and therefore time is critical in immediately stopping the further movement of the bubble towards the patient. A rapid means is therefore desired. In addition, conventional bubble detectors, while recognizing and preventing the introduction of small bubbles may not be as effective when dealing with larger bubbles, i.e., 1.0 cc. or more. In such cases, the larger bubbles may contain sufficient energy (pressure) that even if the pumping system is shut down, the bubble will continue to migrate on its own toward the patient. Therefore, conventional bubble detectors may not be sufficiently effective in containing the larger bubbles and in safeguarding the patient.

A further system, shown in EPO Publication 0,328,162, utilized to detect an open line, or air bubble, relies upon an AC signal being present following an infusion pulse with a ringing effect, however, the ringing effect is not prominent in some systems and an AC signal difficult to detect and analyze.

SUMMARY OF THE INVENTION

In accordance with the present invention a system of bubble detection is presented that has increased speed and effectiveness and which is suitable use for automated systems of injecting liquid into a patient. The system is of particular use with ATD or CCO systems however, it is applicable to any system that features an automatic liquid injection and where the possibility of harm is present from a bubble passing along the liquid delivery line.

In the present system, early bubble detection is made possible by detecting the compressibility of the liquid to be delivered at one or more instants in time, and by comparing that detected parameter indicative of compressibility with a stored value of that liquid with a known compressibility. That is, since the compressibility of the particular liquid in an injection system can be determined and stored, one can determine the presence of a bubble in the pumping means by monitoring and comparing a parameter relating to compressibility against the desired value or values.

Certainly, various parameters can be used or relied upon to evidence compressibility and more that one parameter can be used with the present invention. As an example, the pressure in the outlet of the pumping means can be continuously monitored, and compared to the same pressure readings obtained in the system utilizing a liquid containing no bubbles. Therefore, if a bubble is present, the pressure will be lowerthan that anticipated at a specific time and the system will immediately recognize that the compressibility is a different value than expected, thus the presence of a bubble is recognized and the pumping means immediately disengaged.

Other parameters evidencing compressibility that can be used include the force exerted by the motive means to move the pumping means. In the case of a bubble being present, the force executed against or on the pumping means forcing the liquid toward the patient is less than the force that would ideally be exerted if the bubble, were not present. A simple, yet rapid determination can thus be made by merely monitoring that force at a specific point in time, i.e., 2 seconds after pump initiation. The monitored value of force can thus be simply compared to a stored theshold value and, if the force is less than it should be, the system will recognize a bubble and immediately take corrective action. In this manner, the system obtains an early recognition of a bubble in its initial stages and prior to the bubble entering the passageways leading to the patient.

As a further alternate, the detector could automatically plot the curve of force, pressure or actuating current with respect to time and the first or second derivative of any of those curves could also give an indiction of compressibility. As to the first derivative, the slope of the curve for a compressible fluid abruptly changes after a predetermined period of time, while an incompressible fluid has a characteristic leveling off after that time period. As to the second derivative of those curves, with an incompressible fluid, the rate of change of force, pressure or actuating current is nearly zero followed by a decaying rate of change after a predetermined period of time, i.e., 0.5 seconds.

Thus the slope of those curves or rate of change can be monitored and compared to the data obtained with respect to the slopes of the curves and rates of change of pressure, force or actuating current for the incompressible fluid.

As a further feature of this invention, a redundent system can be utilized wherein two completely independent systems or means can be used to detect the bubbles, thus in the event the system based upon compressibility fails for some reason, a standard bubble detector using photoelectric or ultrasonic detector can be used as a back-up and channeled through separate circuity, electronics and the like. As such, additional safety is assured the patient.

As can be seen, the present bubble detection system based upon detecting and comparing to known values, the compressibility of the fluid to the patient, can be used not only for ATD and CCO systems, but any system having sufficient internal, downstream resistance to effectively validate the data indicating compressibility.

These and other improvements and features of the present invention will become better understood from the detailed description of the preferred embodiments set forth below taken in conjunction with the accompanying drawings.

DETAILED DESCRIPTION OF PREFERRED EMBODIMENT

Figure 1:
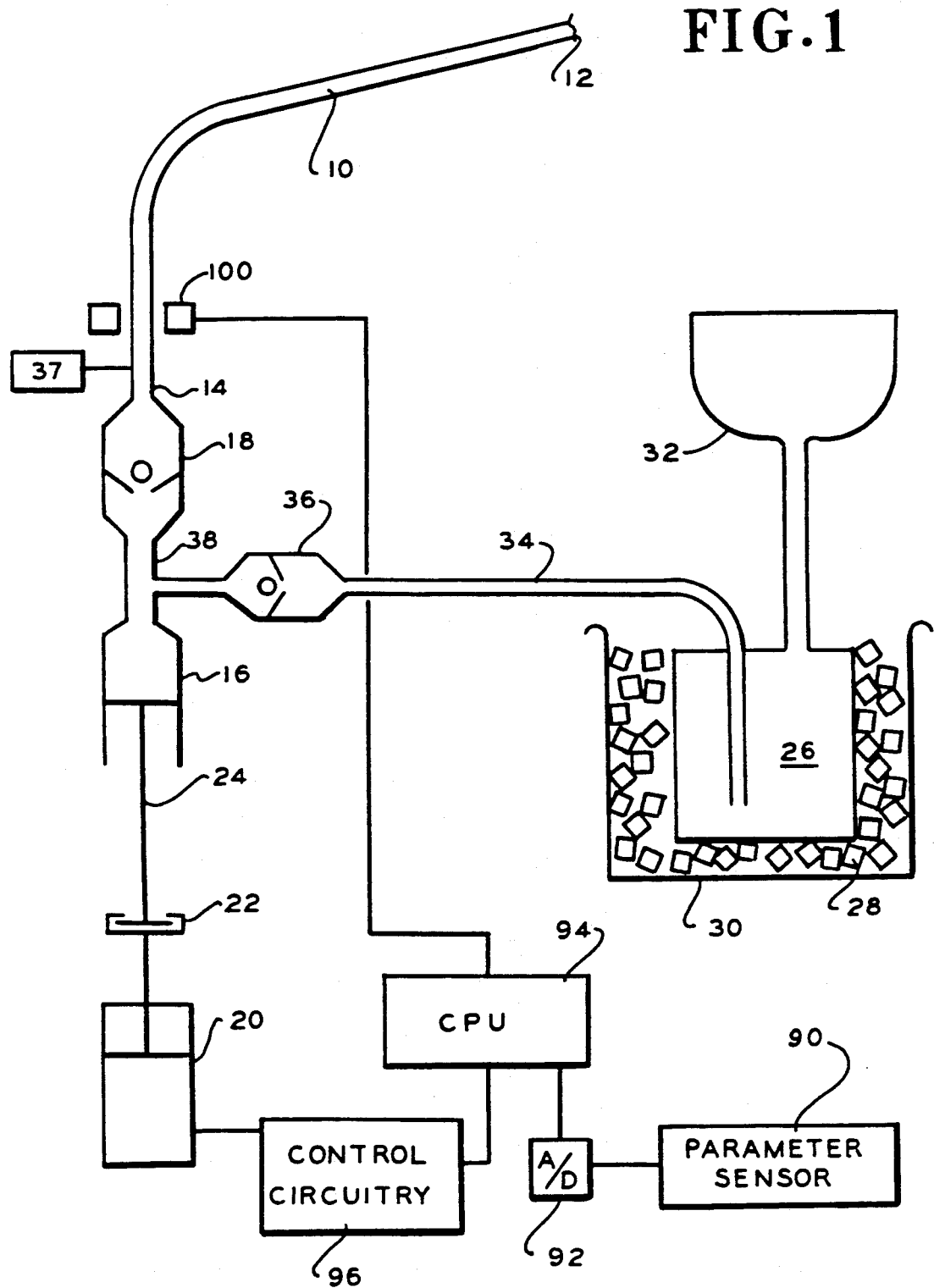
FIG. 1 is a schematic and block diagram of the subject invention.

Turning first to FIG. 1, a schematic, block view is presented of the overall inventive system of bubble detection and includes a conduit 10 having a distal end 12. In the case of ATD, the distal end will be part of a Swan Ganz or other similar type catheter having an opening that allows liquid at a predetermined temperature to be injected into the right atrium of the heart. As will be described that predetermined temperature will be preferred to as chilled, however, any temperature liquid below the patient temperature may be used even room temperature. With CCO, the distal end 12 will connect to a sheath or other heat transfer device that is positioned so as to allow heat transfer with the patient's blood while preventing the chilled liquid of conduit 10 from entering the patient's blood stream.

Other systems may, of course, be adaptable for use with the present invention, however, the present description will refer specifically to a ATD system for convenience.

In its simpliest schematic of FIG. 1, the conduit 10 has a proximal end 14 which is external of the patient and, as shown, receives a bolus of liquid by pump 16 through a check valve 18. Pump 16 in turn, is activated by a motive means 20 and may be of a variety of motive mechanisms such as a linear motor or stepper. A coupling 22 connects the motive means 20 to the plunger 24 of pump 16. Again, typically pump 16 is a commercially available syringe of predetermined capacity.

A supply of chilled liquid is continously available by means of supply container 26 which contains the liquid, such as sterile saline solution, and which is maintained at the proper cold temperature by surrounding supply container 26 with ice 28 contained within larger vessel 30. A reservoir 32 communicates with supply container 26 to maintain an adequate level of chilled liquid.

Supply of the chilled liquid to conduit 10 is provided by an inlet conduit 34 and check valve 36 supplying the liquid to a tee 38 at the outlet of pump 16 but prior to check valve 18. A pressure sensor 37 is located in conduit 10 downstream of check valve 18 to monitor the pressure of fluid being delivered through conduit 10.

As may now be readily seen, in carrying out the operation of the injectate system, the plunger 24 of pump 16 is withdrawn by motive means 20, thereby drawing in a predetermined volume of chilled liquid through inlet conduit 34 and check valve 36 from supply container. In the case of ATD, that volume may be about 5-10 cc's with the liquid at a temperature of between about 35° F. and about 75° F.

When the predetermined volume has been drawn into pump 16, motive means 20 reverses the direction of plunger 24 forcing the bolus of liquid from pump 16 through check valve 18 and into and through conduit 10.

Figure 2:
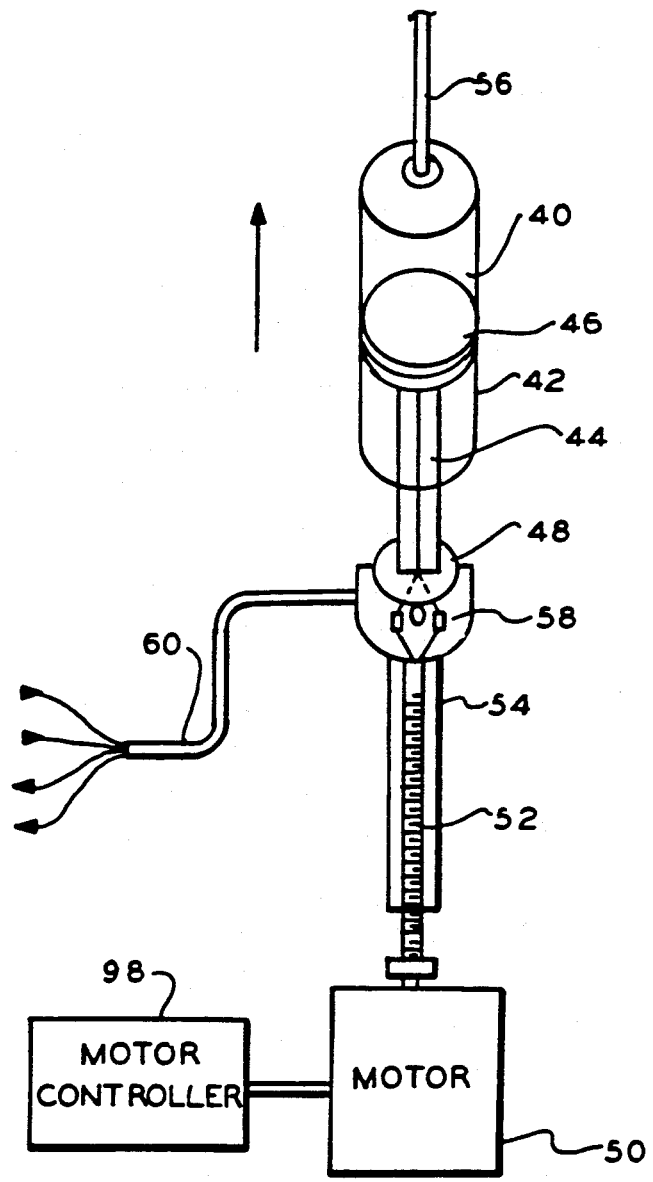
FIG. 2 is a partial perspective and block diagram of one embodiment of the present invention.

Turning briefly to FIG. 2, there is shown in schematic, one arrangement useable in connection with the FIG. 1 system. In FIG. 2, the motor for supplying chilled liquid for the ATD system comprises a syringe 40 having a barrel 42 and a plunger 44. Plunger 44 has a sealed head 46 within barrel 42 and a plunger head 48 external of barrel 42.

Movement of plunger 44 is effected by a motor 50 which may be of a standard stepper motor, such as are available from CompuMotor, Inc. The motor 50 has a threaded shaft 52 depending outwardly therefrom and which engages internal threaded coupler 54 having its external or outward end connected to the plunger head 48.

The rotation of threaded shaft 52 of motor 50 thereby causes the plunger 44 to move within syringe barrel 42 thereby causing chilled liquid to be drawn into syringe 40 as the plunger 44 is withdrawn from syringe 40 or, alternatively, causes the chilled liquid to be forced from syringe 40 into conduit 56 when the plunger 44 is forced into syringe 40.

Obviously, the speed of motor 50 and the thread pitch of motor shaft 52 and coupler 54 determine the relative velocity at which the syringe plunger 44 moves to draw or expel liquid with respect to conduit 56. One can therefore readily design the system of FIG. 2 in order to control the rate of flow and quantity of liquid to be forced into conduit 56 by selecting the proper motor, threads and, of course, size of the particular syringe.

A force measuring device 58 is interposed between coupler 54 and the plunger head 48 of syringe 40 and which measures the force generated between those two members. Typical of such devices are strain gages manufactured by Omega Company, however, any of a variety of strain gauges may be utilized. An electrical cable 60 extends outwardly from force measuring device 58 to communicate the signals for further signal processing means as will be later explained.

Figure 3:
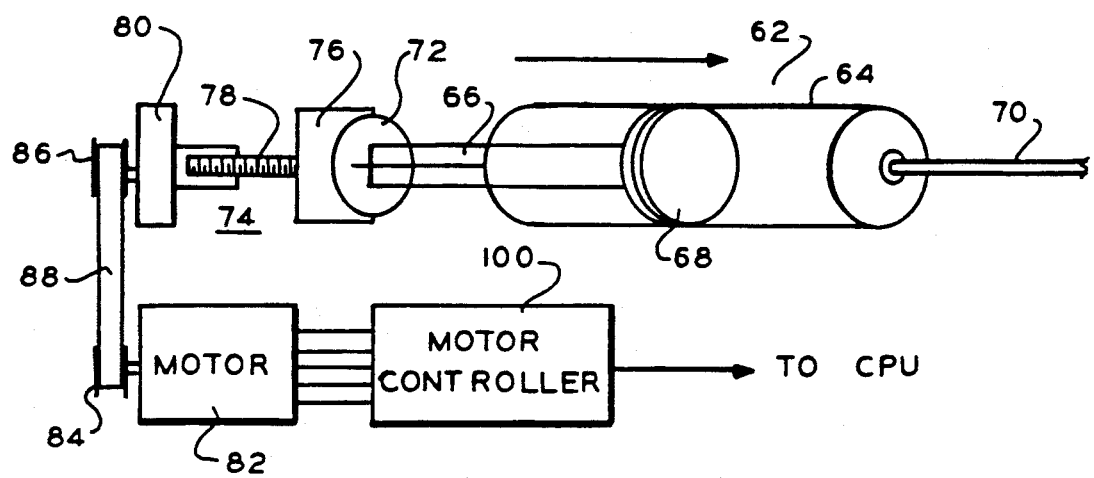
FIG. 3 is a partial perspective and block diagram of another embodiment of the present invention.

Turning now to FIG. 3, an alternate system is disclosed for detecting the compressibility of liquids used with this invention. Again, the set-up of FIG. 3 as used in the FIG. 1 system and includes a syringe 62 including a barrel 64 containing a plunger 66 having a sealed head 68 operatingly moveable within the barrel 64 to draw chilled liquid into syringe 62 from conduit 70 and to force liquid from syringe 62 into conduit 70.

The other end 72 of plunger 66 extends outwardly from the barrel 64 and is affixed to a drive mechanism 74 comprising a fixed head 76 having a threaded shaft 78 which is threadedly engaged in the internal threads of rotatable socket 80. A motor 82 causes rotation of rotatable socket 80 by means of various pulleys 84 and 86 and connecting flexible belt 88. Motors for such application and associated gearheads are commercially available from MicroMo Electronics, Inc., as D.C. micromotors.

Again, as with the FIG. 2 embodiment, the total linear movement of plunger 66 and its rate of movement can readily be controlled by the selection of motor 82, of pulleys 84 and 86 and the threads of threaded shaft 78. In the FIG. 3 embodiment, however, the parameter evidencing compressibility of the liquid being driven from syringe 64 into conduit 70 is the measurement of motor current or power; that is, a specific motor current or power is known to be used in forcing the predetermined quantity of liquid at a specific rate from syringe 64 into conduit 70 and, by comparing the actual sensed readings with the empirically derived values, a difference in compressibility can be recognized and interpreted to be a bubble in the liquid.

Returning to FIG. 1, it can now be seen that the various sensed parameters can be used to indicate the compressibility of the liquid being forced from pump 16. That sensed parameter could be the force exerted by a motive means that is used to compress a syringe (FIG. 2); the current or power used by a motor in a motor operated motive power as in FIG. 3; or the presure of fluid delivered by pump 16 and detected by pressure transducer 37. In either event, some parameter is sensed as the pump 16 is actually forcing the liquid into conduit 10.

That parameter is detected by parameter sensor 90 as, generally, an analog signal. In the event a single value is detected by parameter sensor 90 to be compared with a single stored valve at the same point in time, or central processing unit is not required, the comparison can be carried out with a normal comparator, looking directly at the signal from parameter sensor 90 in analog form. As to multiple signals, however, the analog signal from parameter sensor 90 is then preferably modified to a digital signal by A/D converter 92 before being fed into the central processing unit 94.

CPU 94 contains, in memory, a value or set of values that have been obtained empirically from the use of the pump 16 with a substantially incompressible liquid, that is, a liquid that is administered under supervision and controlled conditions so as to be free of bubbles.

Accordingly, the digital signal representing the sensed parameter from A/D converter 92 is compared in CPU 94 with the same parameter at a similar point or points in time and a determination made on whether or not the liquid then being forced from pump 16 is the same or more compressible than the empirically obtained data. If the CPU 94 determines that the compressibility is the same or substantially the same, the system continues in its normal operation carrying out the forcing of liquid from pump 16 into conduit 10.

In the event, however, that the comparison carried out in CPU 94 determines that the real time measurement indicates that the liquid being delivered by pump 16 is more compressible than the empirically obtained data, CPU 94 recognizes that a bubble is present in that liquid and sends a signal to control circuitry 96 that, in turn operates to stop the further forcing of liquid into conduit 10 to halt the continued movement of that bubble toward a patient and additionally, lowers the pressure of the liquid on the far side of the bubble with respect to the patient.

Reduction of the pressure, in the FIG. 1 schematic would easily be accomplished by immediately reversing the motive means 20 to withdraw plunger 24 thereby drawing the liquid back into pump 16.

In the FIG. 2 and 3 embodiments, motors are utilized and the motor controllers 98 and 100, respectively, may additionally be needed for speed control and to carry out the reversing of the motors however, the motive means for operating a pump to supply liquid in accordance with the present invention might easily be a hydraulic motor or other motive means. Finally, turning to FIG. 4, there is shown various typical curves showing the effect of bubbles on certain parameters and which typlifies the empirical data that can be loaded into the memory of CPU 94 (FIG. 1) . In the FIG. 4 curves, the absissa represents pressure downstream of check valve 18 while the ordinate plots time. The curves represent active data taken using a 50 cc. syringe to force liquid into a typical system with a specific resistance downstream of the pump. The same shape curves would be obtained by measuring force as in the FIG. 2 embodiment, or motor current as in the FIG. 3 embodiment.

The curve a represent the system where the liquid is visually monitored and controlled as to be free of bubbles, while curves b-h represent the same system where controlled bubbles were introduced. Curve B represents the system with a 1 cc. air bubble, curve c with a 2 cc. air bubble, curve d with a 3 cc. air bubble, curve e with a 4 cc. air bubble, curve f with a 5 cc. air bubble, curve g with a 10 cc. air bubble and curve h with a 15 cc. air bubble. The data from curve a can thus be loaded into the CPU memory, either as a single point or as a series of points so as to represent the curve itself.

As an example of a single point system, a point on curve a can be held in a comparator along with a predetermined time following initiation of the pump or syringe to force liquid into a conduit. That time could, for example be 1.5 seconds and the pressure for curve a in the amount of 60 psig. If force is used, a typical force at 1.5 seconds is 50 lbf as a stored value.

As an actual injection of liquid is thus carried out, an actual measurement of the force, pressure or motor current is taken by a strain gage, pressure gage or ammeter at the same point in time (i.e., 1.5 seconds).

The sensed force parameter is then compared in the comparator with the stored value of force and if the values are substantially equal, the injection system is allowed to continue. If, for example, the sensed force is less than the expected value, by perhaps a predetermined amount, the comparator recognizes that a bubble is present and immediately discontinues further forcing of liquid and actually reverses the flow of liquid to draw the bubble in a direction from the patient.

Figure 4:
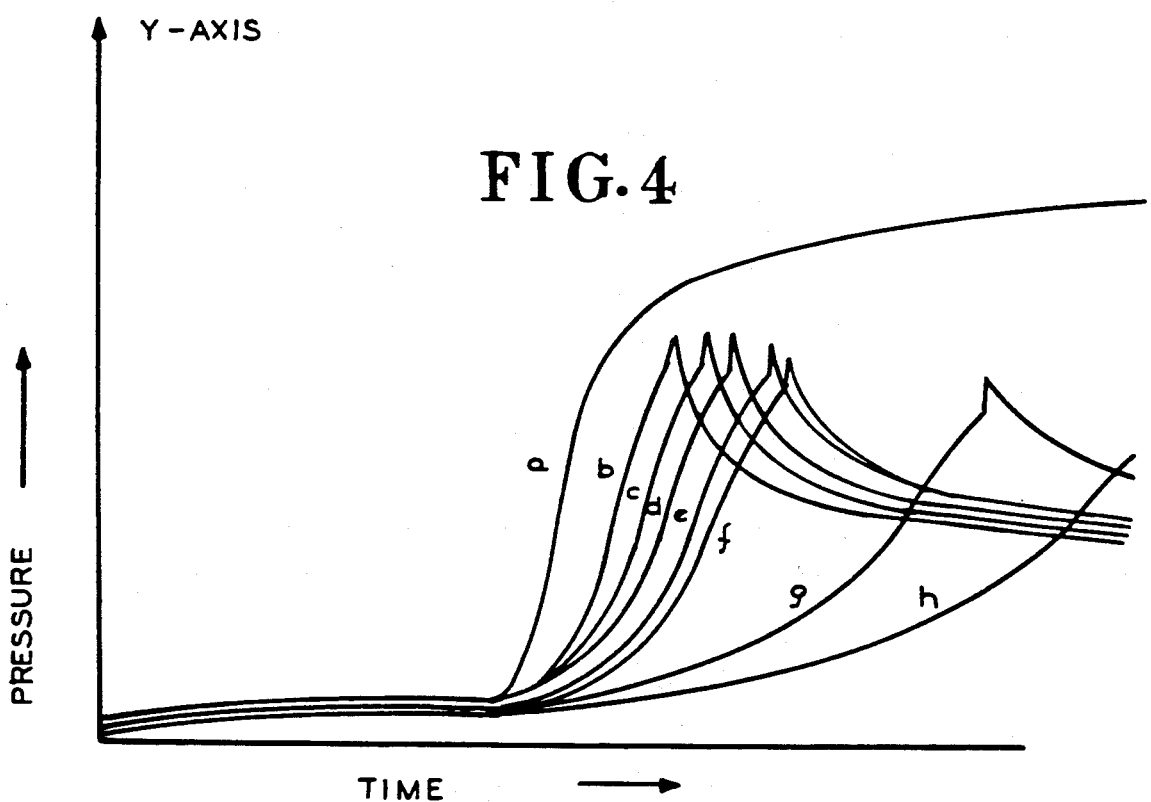
FIG. 4 is a graph evidencing the pressure vs time relationships of an incompressible liquid along with the same liquid containing various sized bubbles.

As an example of the use of a series of data points from the FIG. 4 curves, the actual curves may be sensed, digitized, and compared in the CPU with the empirical curve. The first or second derivative of the curves can be obtained and compared. As can be seen, the difference between first derivative or slope of the curves between curve a and the remaining curves where a bubble is present are distinct. After a predetermined time, the slopes of curves b–h drop rapidly. As to the second derivative, the rate of change in the curve a system has a nearly 0 rate of change up to approximately ½ seconds at which point the rate of change decays and thus is less than 0. The curves representing the presence of bubbles reach a peak and then the rate of change of the curves rapidly break off and as such, a comparison of the curves or points on the various curves readily can distinguish between the substantially incompressible liquid and the liquids that contain bubbles and thus are more compressible.

Again, referring to FIG. 1, the system can also include an optical or ultrasonic type bubble detector 100. A typical optical type is disclosed in U.S. Pat. No. 3,915,155 and thus, for additional protection, a redundent system can be employed to provide added protection to the patient. The bubble detector 100 relies on different circuitry, a different principal of operation and in addition, utilizes a different memory/storage function in the CPU 94, therefore both systems are independent of each other such that failure of one system would not necessarily cause a failure of the other system.

We claim:

1. In a fluid delivery system in which a liquid is delivered through a conduit leading to a patient, a bubble detection means comprising:
   pump means for delivering liquid through the conduit toward the patient;
   control means adapted to control the movement of said pump means;
   detector means adapted to monitor a parameter indicating the compressibility of the liquid delivered through the conduit and to produce at least one signal representing said parameter;
   comparator means for comparing said at least one signal from said detector means with at least one signal of said same parameter indicative of said pump means delivering a known quantity of an incompressible liquid through the conduit at a specific rate, said comparator means producing a signal when said detected signal indicates that the compressibility of the liquid being delivered is a predetermined amount more than that of said compared signal;
   means responsive to said signal from said comparator to discontinue delivering liquid to the patient and to relieve pressure in said conduit.

2. In a fluid delivery system as defined in claim 1 a bubble detection means wherein said pump means comprises a displacement pump driven by an electrical motor and wherein said detector means monitors electrical current to said electrical motor as indicating compressibility.

3. In a fluid delivery system as defined in claim 1, a bubble detection means wherein said detector means monitors the pressure in said conduit of liquid delivered to the patient.

4. In a fluid delivery system as defined in claim 1, a bubble detection means wherein said pump means comprises a displacement pump actuated by a force applied by a linear motor.

5. In a fluid delivery system as defined in claim 4, a bubble detection means wherein said detection means monitors the force applied by said linear motor to power said displacement pump.

6. A bubble detection means for use in a fluid delivery system in which a liquid is delivered through a conduit leading to a patient,
   pump means for delivery liquid through the conduit;
   motive means associated with aid pump for moving said pump to deliver liquid toward said patient;
   control means adapted to control said motive means;
   detector means adapted to monitor a parameter indicating the compressibility of the liquid delivered through the conduit and to produce at least one signal evidencing said parameter;
   memory means having stored therein, at least one signal representative of said monitored parameter indicative of said pump means delivering a known amount of a relatively incompressible fluid through the conduit at a specific known rate;
   comparator means for comparing said at least one signal of said monitored parameter from said detector means with said at least one signal stored in said memory means at predetermined time intervals and to produce a signal when said compared signals indicate that the liquid being delivered through said conduit is more compressible than the relatively incompressible fluid; and
   means responsive to said signal produced from said comparator means to stop said motive means from moving said pump delivering liquid toward said patient.

7. A bubble detection means as defined in claim 6 wherein said at least one signal monitored by said detector means comprises a plurality of signals representing the pressure in said conduit of liquid from said pump means at a plurality of times.

8. A bubble detection means as defined in claim 6 wherein said at least one signal monitored by said detector means comprises a plurality of signals representing electrical current to said motive means.

9. A bubble detection means as defined in claim 6 wherein said motive means exerts a force against said pump means and at least one signal monitored by said detector means comprises a plurality of signals indicative of the force between said motive means and said pump means.

10. A bubble detection means as in claim 6 wherein said memory means contains in its memory, a plurality of signals producing a curve representative of pressure vs. time for of a relatively incompressible liquid forced by said pump means through said conduit and said detector means produces a plurality of signals producing a curve representative of pressure vs. time of the liquid forced through said conduit by said pump means.

11. A bubble detection means as defined in claim 10 wherein said comparator means compares the first derivative of said curve contained in said memory with the first derivative of the curve produced by said detector means.

12. A bubble detection means as defined in claim 10 wherein said comparator means compares the second derivative of said curve contained in said memory with the second derivative of said curve produced by said detector means.

13. A method of preventing large bubbles from entering the blood stream in a patient by traveling along a liquid flow path through a tubing having a distal end within the patient's blood stream and a proximal end external of the patient comprising the steps of:

forcing by motive means the liquid through the tubing in a direction from the proximal end of the tubing toward the distal end within the patient's blood stream;

sensing at least one point in time a parameter indicative of the compressibility of the liquid forced through the tubing and obtaining at least one value for said parameter;

comparing the sensed value of the parameter with a stored value of the same parameter indicative of an incompressible liquid forced by the motive means through said tubing at a predetermined rate into a patient;

discontinuing the motive means where the comparison between the sensed value of the parameter and the stored value indicates that the compressibility of the liquid being forced through the tubing is a predetermined amount more compressible than an incompressible liquid; and relieving the pressure in said flow path at or about the proximal end of the tubing.

14. A method as defined in claim 13 wherein said sensing step comprises sensing said parameters at a plurality of points in time to obtain a plurality of values.

15. A method as defined in claim 14 wherein said sensing step comprises sensing the pressure in said tubing.

16. A method as defined in claim 13 wherein said step of forcing by motive means comprises providing an electrical motive means and a pump means operable by said electrical motive means and said sensing step comprises sensing the electrical current to the electrical motive means.

17. A method as defined in claim 13 wherein said step of forcing by motive means comprises providing an actuator means and a piston pump operated by a force exerted by said actuator means.

18. A method as defined in claim 17 wherein said sensing step comprises sensing the force between said actuator means and said piston pump.

19. A bubble detection means for use in a fluid delivery system in which a liquid is delivered through a conduit leading to a patient;

pump means for delivering liquid through the conduit;

motive means associated with said pump for moving said pump to deliver liquid toward said patient;

control means adapted to control said motive means;

detector means adapted to monitor a parameter indicating the compressibility of the liquid delivered through the conduit and to produce at least one signal evidencing said parameter;

a central processor unit having as a first function, a memory means, said memory means having stored therein, at least one signal representative of said monitored parameter for said pump means delivering a known amount of a relatively incompressible fluid through the conduit at a predetermined rate;

comparator means for comparing said at least one signal of said monitored parameter from said detector means with said at least one signal stored in said memory means at predetermined time intervals and to produce a signal when said compared signals indicate that the liquid being delivered through said conduit is more compressible than the relatively incompressible fluid;

an independent bubble detector means located in said conduit and detecting bubbles in said liquid delivered from said pump means; said independent bubble detector utilizing a second function of said central processor unit to produce a signal when a bubble is detected; and means responsive to said signal produced from said comparator means and said signal from said second function of said central processor unit to stop said motive means from moving said pump delivering liquid toward said patient.

20. A bubble detection means as defined in claim 19 wherein said pump means comprises a cylinder and a piston moveable therein to deliver liquid through the conduit.

21. A bubble detection means as defined in claim 20 wherein said detector means monitors the pressure of liquid within said conduit at a predetermined time and said comparator means compares said monitored pressure signal with a stored value of pressure at said same predetermined time and produces a signal when said monitored value is a predetermined amount lower than said stored signal.

22. A bubble detector means as defined in claim 21 wherein said means responsive to said signal produced from said comparator means and said second function of said central processor unit stops said piston and reverses the direction of said piston to draw liquid in a direction from the patient.

23. A bubble detection means as defined in claim 20 wherein said motive means comprises an electric motor and said detector means monitors the electrical current to said motor at a plurality of times.

24. A bubble detector means as defined in claim 23 wherein said memory means has stored therein a curve representing electrical current vs. time for operation of said pump means with a relatively incompressible fluid.

25. A bubble detection means as defined in claim 20 wherein said motive means comprises a linear motor creating a force against said piston to deliver said liquid and said detector means monitors the amount of force executed by said linear motor against said piston at a plurality of times.

26. A bubble detector means as defined in claim 25 wherein said memory means has stored therein a curve representing the force vs. time of the force exerted by said linear motor against said piston for operation of said pump means with a relatively incompressible fluid.

* * * * *